(12) United States Patent
Rodecker (10) Patent No.: US 7,644,911 B2
(45) Date of Patent: Jan. 12, 2010

(54) ISOLATOR

(75) Inventor: Troy P. Rodecker, Berlin Heights, OH (US)

(73) Assignee: The Pullman Company, Milan, OH (US)

( * ) Notice: Subject to any disclaimer, the term of this patent is extended or adjusted under 35 U.S.C. 154(b) by 817 days.

(21) Appl. No.: 11/233,283

(22) Filed: Sep. 22, 2005

(65) Prior Publication Data

US 2007/0063401 A1 Mar. 22, 2007

(51) Int. Cl.
*F16F 9/00* (2006.01)
(52) U.S. Cl. .................... 267/293; 267/140.12
(58) Field of Classification Search ..............
267/140.12–140.13, 140, 292–294; 248/59, 248/60, 603–621
See application file for complete search history.

(56) References Cited

U.S. PATENT DOCUMENTS

| | | | |
|---|---|---|---|
| 3,977,486 A | 8/1976 | Kleinschmit | |
| 4,019,599 A | 4/1977 | Strunk | |
| 4,063,700 A | 12/1977 | Brewer | |
| 4,494,722 A | 1/1985 | Kanai et al. | |
| 4,550,795 A | 11/1985 | Teshima | |
| 4,634,088 A | 1/1987 | Schad | |
| 4,638,965 A | 1/1987 | De Bruine et al. | |
| 4,705,410 A * | 11/1987 | von Broock | 384/99 |
| 4,796,841 A | 1/1989 | Baker et al. | |
| 4,824,056 A | 4/1989 | Wuebker et al. | |
| 4,893,778 A | 1/1990 | Drabing et al. | |
| 4,893,799 A * | 1/1990 | de Fontenay | 267/140.12 |
| 5,127,489 A | 7/1992 | Takato et al. | |
| 5,152,510 A | 10/1992 | Komabashiri | |
| 5,284,315 A | 2/1994 | Hofmann et al. | |
| 5,323,989 A | 6/1994 | Hamada et al. | |
| 5,445,241 A | 8/1995 | Nakamura et al. | |
| 5,507,463 A | 4/1996 | Kobylinski et al. | |
| 5,890,685 A | 4/1999 | Takahashi | |
| 5,908,187 A | 6/1999 | Kalkoske et al. | |
| 6,070,849 A | 6/2000 | Larmande et al. | |
| 6,402,119 B1 | 6/2002 | Miska | |
| 6,659,438 B2 * | 12/2003 | Michael et al. | 267/294 |
| 6,758,300 B2 | 7/2004 | Kromis et al. | |
| 2004/0135287 A1 | 7/2004 | Kries et al. | |
| 2005/0194728 A1 | 9/2005 | Molet et al. | |
| 2007/0065062 A1 | 3/2007 | Roth | |

FOREIGN PATENT DOCUMENTS

GB 2 430 239 4/2008

OTHER PUBLICATIONS

Written Opinion dated Mar. 25, 2009 from corresponding Singapore Application No. 0801323-7.
Examination Report dated Sep. 18, 2009 from corresponding United Kingdom Application No. GB0802561.1.

* cited by examiner

*Primary Examiner*—Christopher P Schwartz
(74) *Attorney, Agent, or Firm*—Harness, Dickey & Pierce, PLC (57) ABSTRACT

An elastomeric isolator has an elastomeric body which defines a void extending into the elastomeric body from one side and a void extending into the elastomeric body from the opposite side. One member for attaching the elastomeric body to a component is located inside of the two voids and another member for attaching the elastomeric body to a component is located outside of the two voids. The two voids overlap a specified distance to determine the stresses and stiffness for the isolator.

19 Claims, 12 Drawing Sheets

FIG - 23 ns ISOLATOR

FIELD OF THE INVENTION

The present invention relates to an automotive exhaust system isolator. More particularly, the present invention relates to an isolator which is configured to provide a very soft on-center rate but yet have the ability to endure spike durability loads.

BACKGROUND OF THE INVENTION

Typically, automotive vehicles including cars and trucks have an internal combustion engine which is coupled to at least a transmission and a differential for providing power to the drive wheels of the vehicle. An engine exhaust system which typically includes an exhaust pipe, a catalytic converter and a muffler is attached to the engine to quiet the combustion process, to clean the exhaust gases and to route the products of combustion away from the engine to a desired position typically at the rear of the vehicle. The exhaust system is supported by exhaust mounts which are positioned between the exhaust system and the frame or some other supporting structure of the vehicle body. In order to prevent engine vibrations from being transmitted to the car body, the exhaust mounts incorporate flexible members or elastic suspension members to isolate the vehicle's exhaust system from the vehicle's body. In order to effectively isolate the vehicle's exhaust system from the vehicle's body, it is preferred that the isolator include a soft on-center rate of deflection.

The prior art exhaust mounts or isolators have included rubber isolators which are a solid rubber component or a puck that is at least three-quarters of an inch thick and which is provided with at least one pair of apertures extending therethrough. The apertures each receive an elongated metal stud. The metal stud is provided with an enlarged head that can be forced through the aperture in the isolator, but it cannot be readily removed from the isolator. The opposite end of the stud is welded to or otherwise secured to either a support point in the vehicle or to one of the components of the exhaust system.

Other designs for isolators include elastomeric moldings of a spoke design where spokes are loaded in tension and compression and a shear leg design that include a leg that is subjected to shearing in the primary loading direction. Most elastomers which are utilized for exhaust isolators exhibit poor tensile fatigue properties stemming from low tear strength properties. The preferred method to load the elastomeric material is in compression or shear.

The prior art puck design is the simplest design, and as discussed above, two pins are inserted at opposite ends of the elastomer and the loads inflict pure tension on the elastomer cords connecting both ends. While this is typically the lowest cost design, it is also the most abusive to the material. In order to offset the failure risk, flexible or rigid bands are typically designed inside or around the outside of the elastomeric puck. The advantage of this design is its ability to swivel about one hanger hole to accommodate large positional tolerances for the hanger.

The prior art spoke design isolators load the elastomeric material in compression and tension. The tensile loading makes the design vulnerable to fractures in overloaded conditions. The stress magnitude is directly proportional to the load divided by the minimum spoke cross-sectional area. An additional requirement of the spoke design is that the mating component or hanger pin be positioned within the deflection zone. If it is not, the voids designed into the isolator will be bottomed out or positioned in a groundout condition. This results in the soft on-center rate not being employed, thus defeating the purpose of the isolator.

The prior art shear leg design has a primary loading direction which is typically vertical and a secondary loading direction which is typically lateral. When the shear leg design is loaded in its primary loading direction, the loading method is the shear style loading. In addition, this shear style loading is able to be designed desirably soft. However, the secondary loading direction inflicts tensile compressive stresses which are unfavorable for durability. In addition, the secondary loading direction has a rate that is two to three times stiffer than the primary rate which is also an unfavorable condition.

The continued development of elastomeric mounts has been directed to elastomeric mounts which include a soft on-center rate while avoiding the undesirable tension loading of the elastomeric bushing.

SUMMARY OF THE INVENTION

The present invention provides the art with an elastomeric bushing which uses radial loading to avoid the tension stress loading of the bushing. The radial loading cause shear stresses of the elastomeric bushing regardless of the direction of the loading. Tuning for rate and deflection in specific directions can be independent from other directions by altering voids in the elastomeric bushings.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

Figure 23:
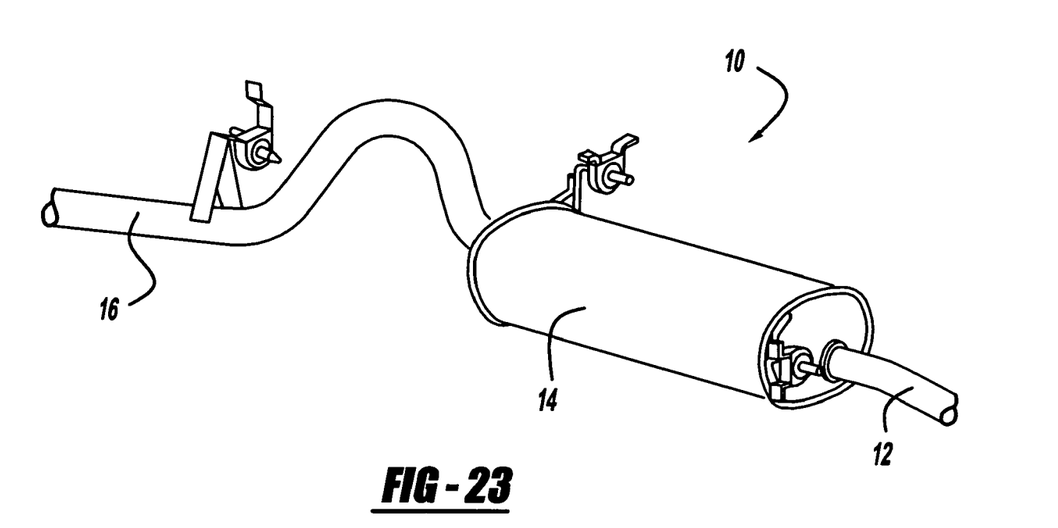
FIG. 23 is a perspective view of an exhaust system which incorporates the unique exhaust isolators in accordance with the present invention.

Referring now to the drawings, there is shown in FIG. 23 an exhaust system which includes the exhaust system isolators in accordance with the present invention and which is designated generally by the reference numeral 10. A typical vehicle comprises an internal combustion engine (not shown), a body (not shown), a suspension system (not shown) and exhaust system 10 which is attached to the internal combustion engine and which is supported typically beneath the vehicle. The internal combustion engine is designed to power one or more drive wheels of the vehicle and the exhaust system routes the products of combustion to a desired exhaust location around the outside of the vehicle.

Exhaust system 10 comprises an intermediate pipe 12, a muffler 14, a tailpipe 16 and a plurality of isolator assemblies of various designs. Intermediate pipe 12 is typically connected to the engine or to a catalytic converter (not shown) which is then attached to an exhaust pipe which extends between the engine and the catalytic converter. The catalytic converter may be attached to a single exhaust pipe which leads to a single exhaust manifold or the catalytic converter can be attached to a branched exhaust pipe which leads to a plurality of exhaust pipes which lead to a plurality of exhaust manifolds. Also, intermediate pipe 12 can be attached to a plurality of catalytic converters which connect together prior to reaching muffler 14 using intermediate pipe 12 or the vehicle can have a plurality of exhaust pipes, a plurality of catalytic converters, a plurality of intermediate pipes 12 and a plurality of mufflers 14 which connect together using a single or multiple tailpipes 16. In addition, the exhaust system isolator of the present invention is applicable to any type of exhaust system including but not limited to dual exhaust system which have two separate parallel exhaust systems extending from the internal combustion system.

Exhaust system 10 is utilized to route the exhaust gases from the engine to a desired location around the outside of the vehicle. While traveling through the exhaust system, the catalytic converter cleans the exhaust gases and muffler 14 quiets the noise created during the combustion process in the engine. The present invention is directed toward the exhaust system isolators which mount exhaust system 10 to the vehicle while at the same time, isolate the movement of exhaust system 10 with respect to the vehicle.

Referring now to FIGS. 1-4, an exhaust system isolator 30 in accordance with the present invention is illustrated. Isolator 30 comprises an elastomeric body 32 within which a reinforcement inner metal 34 is molded. Isolator 30 is a two-hole shear hub design where elastomeric body 32 defines a pair of holes 36 and 38 which are designed to accept a pair of inner tubes or hanger pins 40 and 42. One of hanger pins 40 or 42 is secured to the frame or the mounting structure of the vehicle and the other hanger pin 40 or 42 is secured to exhaust system 10. Thus, exhaust system 10 is secured to the vehicle through isolator 30.

Figure 1:
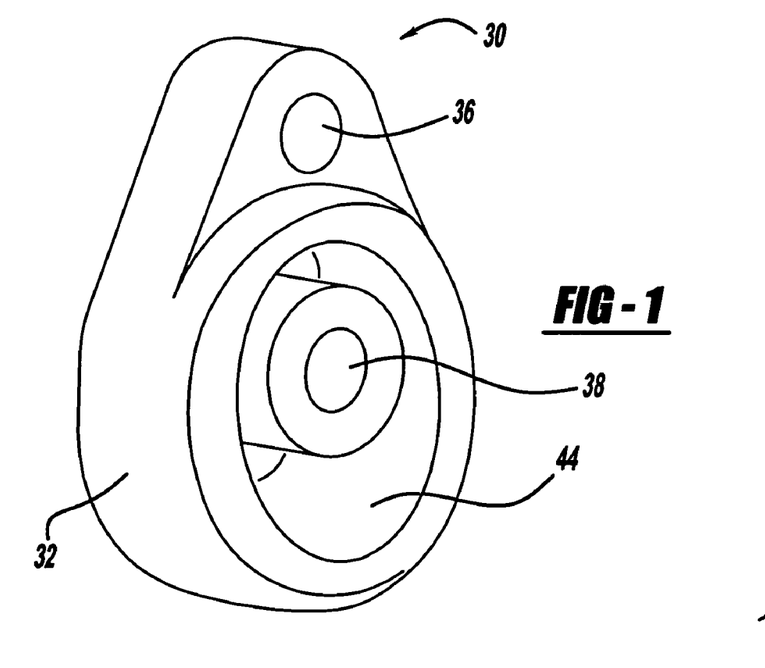
FIG. 1 is a perspective view of an elastomeric isolator in accordance with the present invention.
Figure 2:
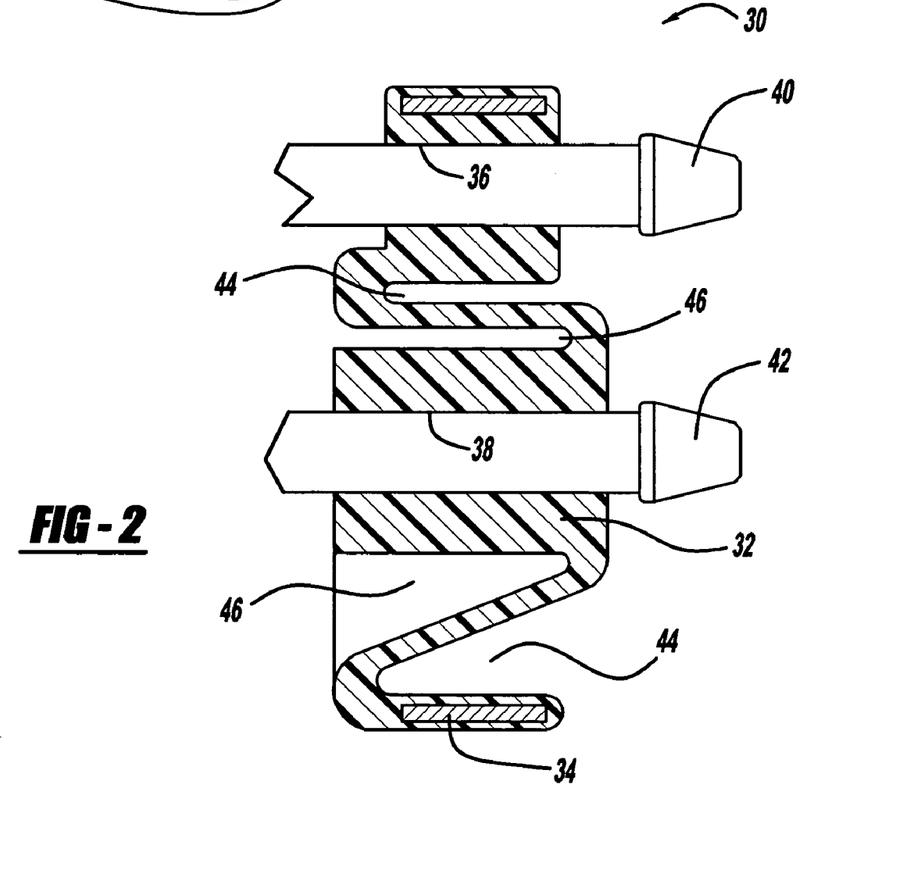
FIG. 2 is a cross-sectional view of the elastomeric isolator illustrated in FIG. 1.
Figures 3, 4:
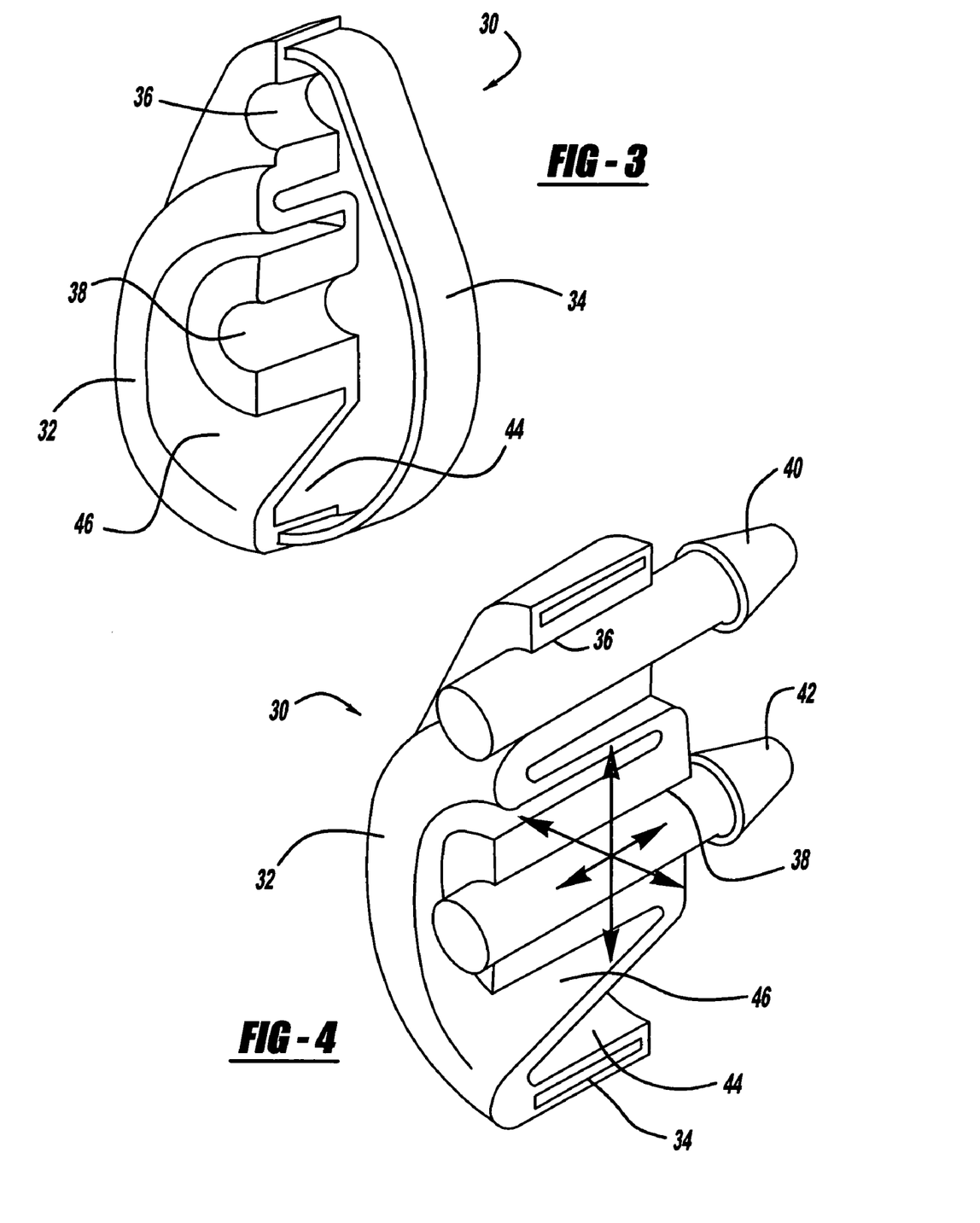
FIG. 3 is a perspective view partially in cross-section illustrating the inner metal of the elastomeric isolator illustrated in FIG. 1.
FIG. 4 is a perspective view partially in cross-section illustrating the directions of isolation for the elastomeric isolator illustrated in FIG. 1.

Elastomeric body 32 defines an outer circumferential void 44 and an inner circumferential void 46. While voids 44 and 46 are illustrated as asymmetrical with respect to the center of hole 38, it is within the scope of the present invention to have voids 44 and 46 symmetrical with respect to hole 38 if desired. The design of the voids, specifically their thickness, will determine the amount of travel until the rate of the bushing spikes up due at the closing of the voids. Until the closing of the voids, the radial loads cause pure shear regardless of the loading direction. As illustrated in FIG. 4, the loading direction can be in any one of the three axial directions. Tuning for rate and deflection in selective directions can be accomplished independently from other directions by altering voids 44 and 46 in the required sectors. As can be seen in FIG. 2, void 44 overlaps with void 46. The larger the overlap between voids 44 and 46, the lower the stresses and stiffness for isolator 30. The peak loads bottom out voids 44 and 46 and start to impart compressive stress to elastomeric body 32 from hanger pins 40 and/or 42 and inner metal 34 by sandwiching. As illustrated in FIG. 3, inner metal 34 extends around the periphery of elastomeric body 32. The bottoming out of voids 44 and 46 and subsequent compression of elastomeric body 32 makes the stress spread out to all of the material between hanger pins 40 and 42 and inner metal 34 rather than having the stress concentrated in a spoke or leg cross-section as in the prior art. This permits the stress magnitude to decrease as well as changing the stress loading to a more favorable type.

Thus, exhaust system isolator 30 provides a very soft on-center rate which is desirable with the ability to endure spike durability loads after closing of the voids.

Figures 5, 6:
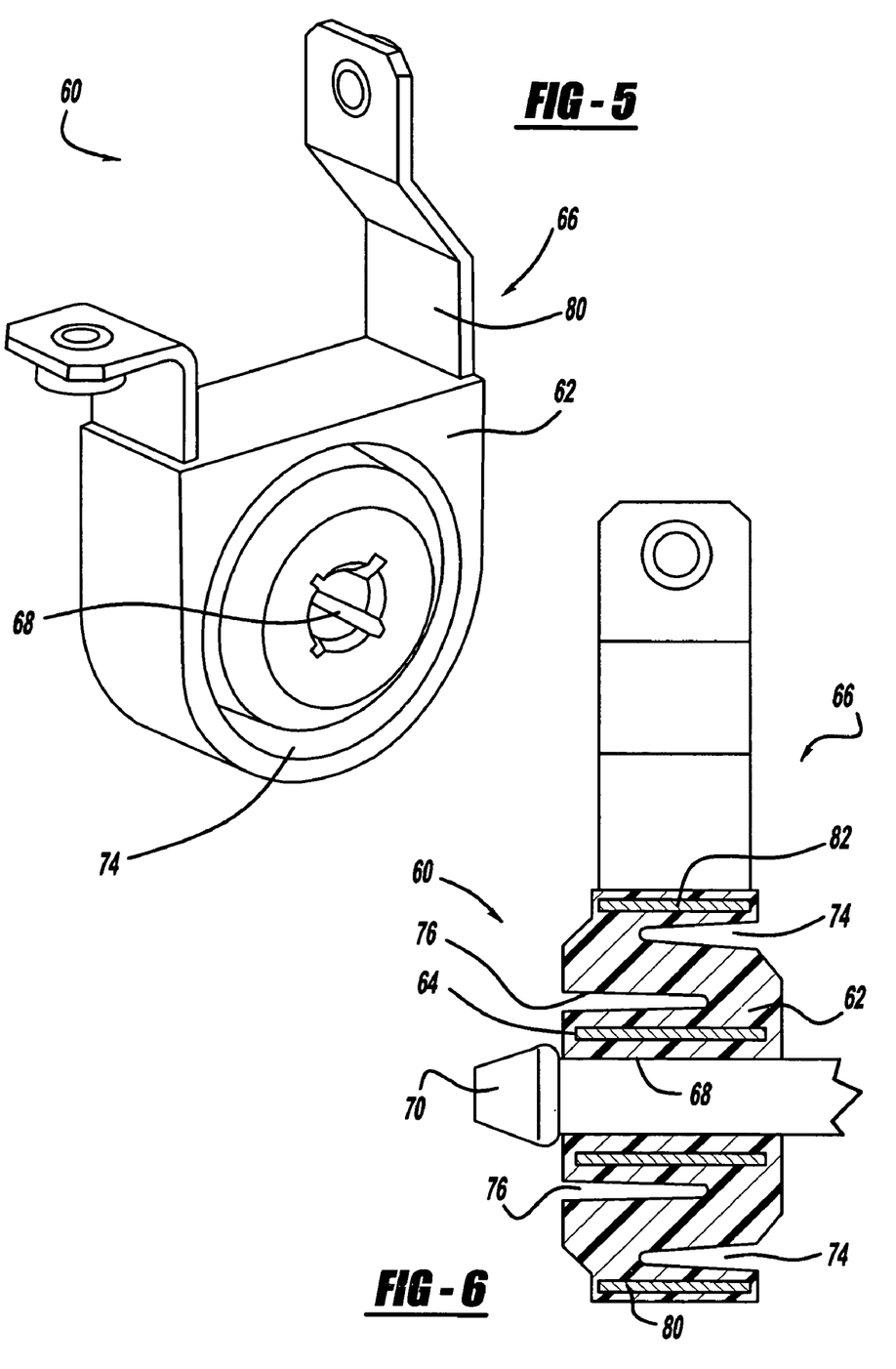
FIG. 5 is a perspective view of an elastomeric isolator in accordance with another embodiment of the present invention.
FIG. 6 is a cross-sectional view of the elastomeric isolator illustrated in FIG. 5.

Referring now to FIGS. 5 and 6, an exhaust system isolator 60 in accordance with another embodiment of the present invention is illustrated. Isolator 60 comprises an elastomeric body 62 within which an inner reinforcement 64 and an outer reinforcement 66 are molded. Isolator 60 is a single hole shear hub design where elastomeric body 62 defines a hole 68 which is designed to accept an inner tube or hanger pin 70. Hanger pin 70 is secured to exhaust system 10 and isolator 60 is secured to the frame or the mounting structure of the vehicle using outer reinforcement 66. Thus, exhaust system 10 is secured to the vehicle through isolator 60.

Elastomeric bushing 62 defines an outer circumferential void 74 and an inner circumferential void 76. While voids 74 and 76 are illustrated as symmetrical with respect to the center of hole 68, it is within the scope of the present invention to have voids 74 and 76 asymmetrical with respect to hole 68 if desired. The design of the voids, specifically their thickness, will determine the amount of travel until the rate of the bushing spikes up at the closing of the voids. Until the closing of the voids, the radial loads cause pure shear regardless of the loading direction. Similar to that discussed above for isolator 30, isolator 60 can be loaded in any of the three axial directions illustrated in FIG. 4. Tuning for rate and deflection in selective directions can be accomplished independently from other directions by altering voids 74 and 76 in the required sectors. As can be seen in FIG. 6, void 74 overlaps with void 76. The larger the overlap between voids 74 and 76, the lower the stresses and stiffness for isolator 60. Voids 74 and 76 are located between inner reinforcement 64 and outer reinforcement 66 such the peak loads bottom out voids 74 and 76 and start to impart compressive stress to elastomeric body 62 from inner reinforcement 64 and outer reinforcement 66 by sandwiching. As illustrated in FIGS. 5 and 6, outer reinforcement 66 comprises a generally U-shaped bracket 80 which is adapted to be secured to the frame or the mounting structure of the vehicle and a generally straight bracket 82 which extends between the two legs or U-shaped bracket 80 and is secured to each leg of U-shaped bracket 80 by crimping or by any other means known in the art. Thus, the bottoming out of voids 74 and 76 and subsequent compression of elastomeric body 62 makes the stress spread out to all of the material between inner reinforcement 64 and outer reinforcement 66 as well as between hanger pin 70 and inner reinforcement 64 rather than having the stress concentrated in a spoke or leg cross-section as in the prior art. This permits the stress magnitude to decrease as well as changing the stress loading to a more favorable type.

Thus, exhaust system isolator 60, similar to isolator 30, provides a very soft on-center rate which is desirable with the ability to endure spike durability loads after closing of the voids.

Figures 7, 8:
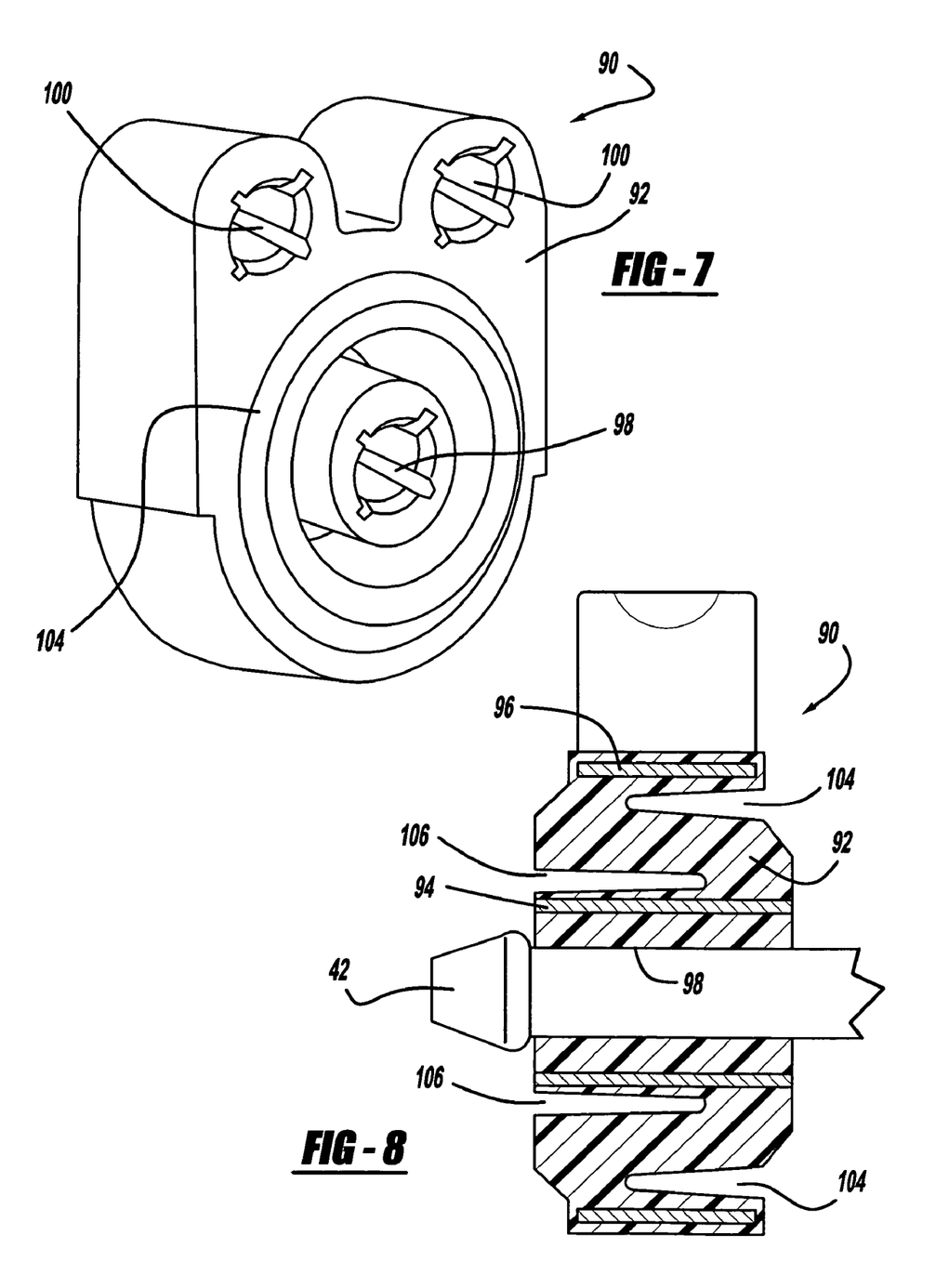
FIG. 7 is a perspective view of an elastomeric isolator in accordance with another embodiment of the present invention.
FIG. 8 is a cross-sectional view of the elastomeric isolator illustrated in FIG. 7.

Referring now to FIGS. 7 and 8, an exhaust system isolator 90 in accordance with another embodiment of the present invention is illustrated. Isolator 90 comprises an elastomeric body 92 within which an inner reinforcement 94 and an outer reinforcement 96 are molded. Isolator 90 is a three-hole shear hub design where elastomeric body 92 defines a centrally located hole 98 which is designed to accept a single hanger pin 42 which is secured to exhaust system 10 and a pair of holes 100 which are each designed to accept a hanger pin 40. Each hanger pin 40 is secured to the frame or mounting structure of the vehicle. Thus, exhaust system 10 is secured to the vehicle through isolator 90. By using two hanger pins 40, anti-rotation is provided to isolator 90 to support the three degrees of freedom or motion of hanger pin 42 as illustrated in FIG. 4 for isolator 30.

Elastomeric body 92 defines an outer circumferential void 104 and an inner circumferential void 106. While voids 104 and 106 are illustrated as symmetrical with respect to the center of hole 98, it is within the scope of the present invention to have voids 104 and 106 asymmetrical with respect to hole 98 if desired. The design of the voids, specifically their thickness, will determine the amount of travel until the rate of the bushing spikes up due at the closing of the voids. Until the closing of the voids, the radial loads cause pure shear regardless of the loading direction. As illustrated in FIG. 4, the loading direction can be in any one of the three axial directions. Tuning for rate and deflection in selective directions can be accomplished independently from other directions by altering the voids in the required sectors. As can be seen in FIG. 8, void 104 overlaps with void 106. The larger the overlap between voids 104 and 106, the lower the stresses and stiffness for isolator 90. The peak loads bottom out voids 104 and 106 and start to impart compressive stress to elastomeric body 92 from voids 104 and 106 are located between inner reinforcement 94 and outer reinforcement 96 such that peak loads bottom out voids 104 and 106 and start to impart compressive stress to elastomeric body 92 from inner reinforcement 94 and outer reinforcement 96 by sandwiching. As illustrated in FIGS. 7 and 8, inner reinforcement 94 extends around hole 98 and outer reinforcement 96 extends around the periphery of elastomeric body 92. Thus, the bottoming out of voids 104 and 106 and subsequent compression of elastomeric body 92 makes the stress spread out to all of the material between inner reinforcement 94 and outer reinforcement 96 as well as between hanger pin 42 and inner reinforcement 94 and outer reinforcement 96 and hanger pins 42. This is preferred over the stress concentrated in a spoke or leg cross-section as in the prior art. This permits the stress magnitude to decrease as well as changing the stress loading to a more favorable type.

Thus, exhaust system isolator 90, similar to isolator 30, provides a very soft on-center rate which is desirable with the ability to endure spike durability loads after closing of the voids.

Figure 9:
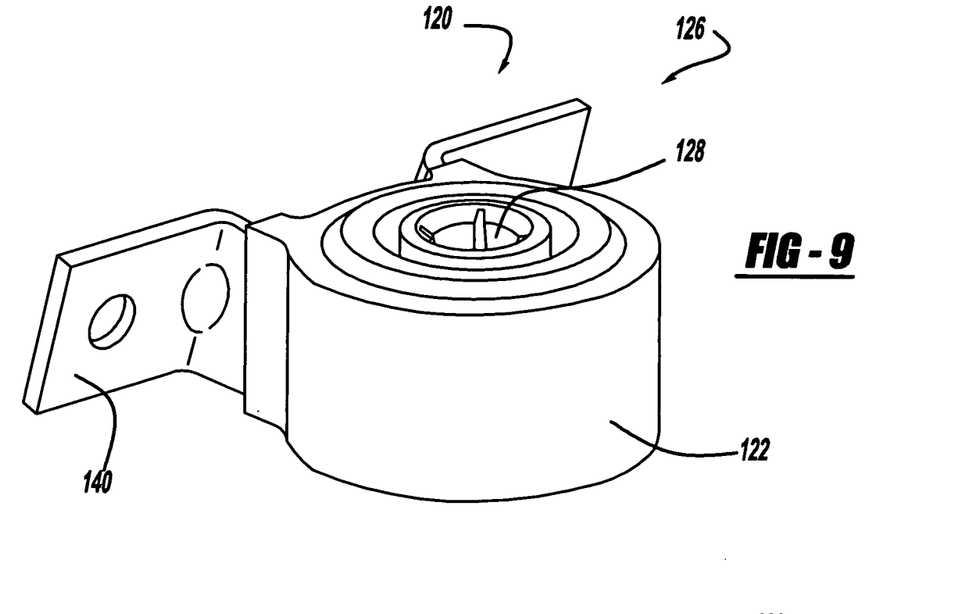
FIG. 9 is a perspective view of an elastomeric isolator in accordance with another embodiment of the present invention.
Figure 10:
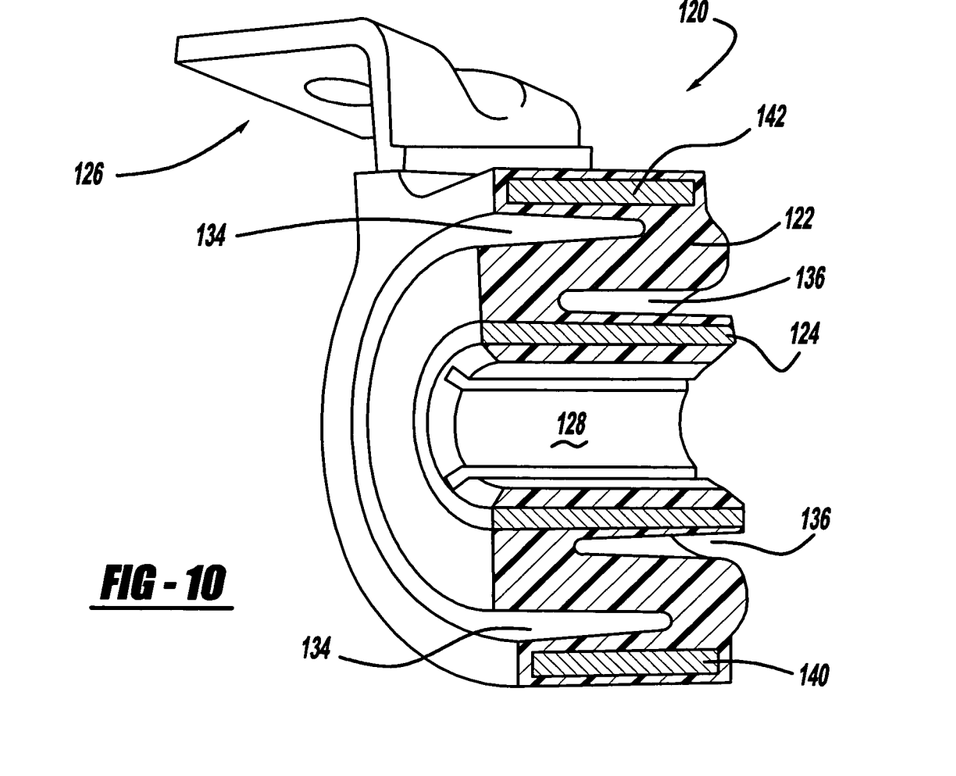
FIG. 10 is a cross-sectional view of the elastomeric isolator illustrated in FIG. 9.

Referring now to FIGS. 9 and 10, an exhaust system isolator 120 in accordance with another embodiment of the present invention is illustrated. Isolator 120 comprises an elastomeric body 122 within which an inner reinforcement 124 and an outer reinforcement 126 are molded. Isolator 120 is a hole shear hub design where elastomeric body 122 defines a hole 128 which is designed to accept an inner tube or hanger pin 42. Hanger pin 42 is secured to exhaust system 10 and isolator 120 is secured to the frame or the mounting structure of the vehicle using outer reinforcement 126. Thus, exhaust system 10 is secured to the vehicle through isolator 120.

Elastomeric bushing 122 defines an outer circumferential void 134 and an inner circumferential void 136. While voids 134 and 136 are illustrated as symmetrical with respect to center of hole 128, it is within the scope of the present invention to have voids 134 and 136 asymmetrical with respect to hole 128 if desired. The design of the voids, specifically their thickness will determine the amount of travel until the rate of the bushing spikes up at the closing of voids 134 and 136. Until the closing of voids 134 and 136, the radial loads cause pure shear regardless of the loading direction. Similar to that discussed above for isolator 30, isolator 120 can be loaded in any of the three axial directions as shown in FIG. 4. Tuning for rate and deflection in selective directions can be accomplished independently from other directions by altering voids 134 and 136 in the required sectors. As can be seen in FIG. 10, void 134 overlaps with void 136. The larger the overlap between voids 134 and 136, the lower the stresses and stiffness for isolator 60. Voids 134 and 136 are located between inner reinforcement 124 and outer reinforcement 126 such the peak loads bottom out voids 134 and 136 and start to impart compressive stress to elastomeric body 132 from inner reinforcement 134 and outer reinforcement 136 by sandwiching. As illustrated in FIGS. 9 and 10, outer reinforcement 126 comprises a generally U-shaped bracket 140 which is adapted to be secured to the frame or the mounting structure of the vehicle and a bracket 142 which extends between the two legs or U-shaped bracket 140 and is secured to each leg of U-shaped bracket 140 by crimping or by any other means known in the art. Thus, the bottoming out of voids 134 and 136 and subsequent compression of elastomeric body 122 makes the stress spread out to all of the material between inner reinforcement 124 and outer reinforcement 126 as well as between hanger pin 42 and inner reinforcement 124 rather than having the stress concentrated in a spoke or leg cross-section as in the prior art. This permits the stress magnitude to decrease as well as changing the stress loading to a more favorable type.

Thus, exhaust system isolator 120, similar to isolator 30, provides a very soft on-center rate which is desirable with the ability to endure spike durability loads after closing of the voids.

Figures 11, 12:
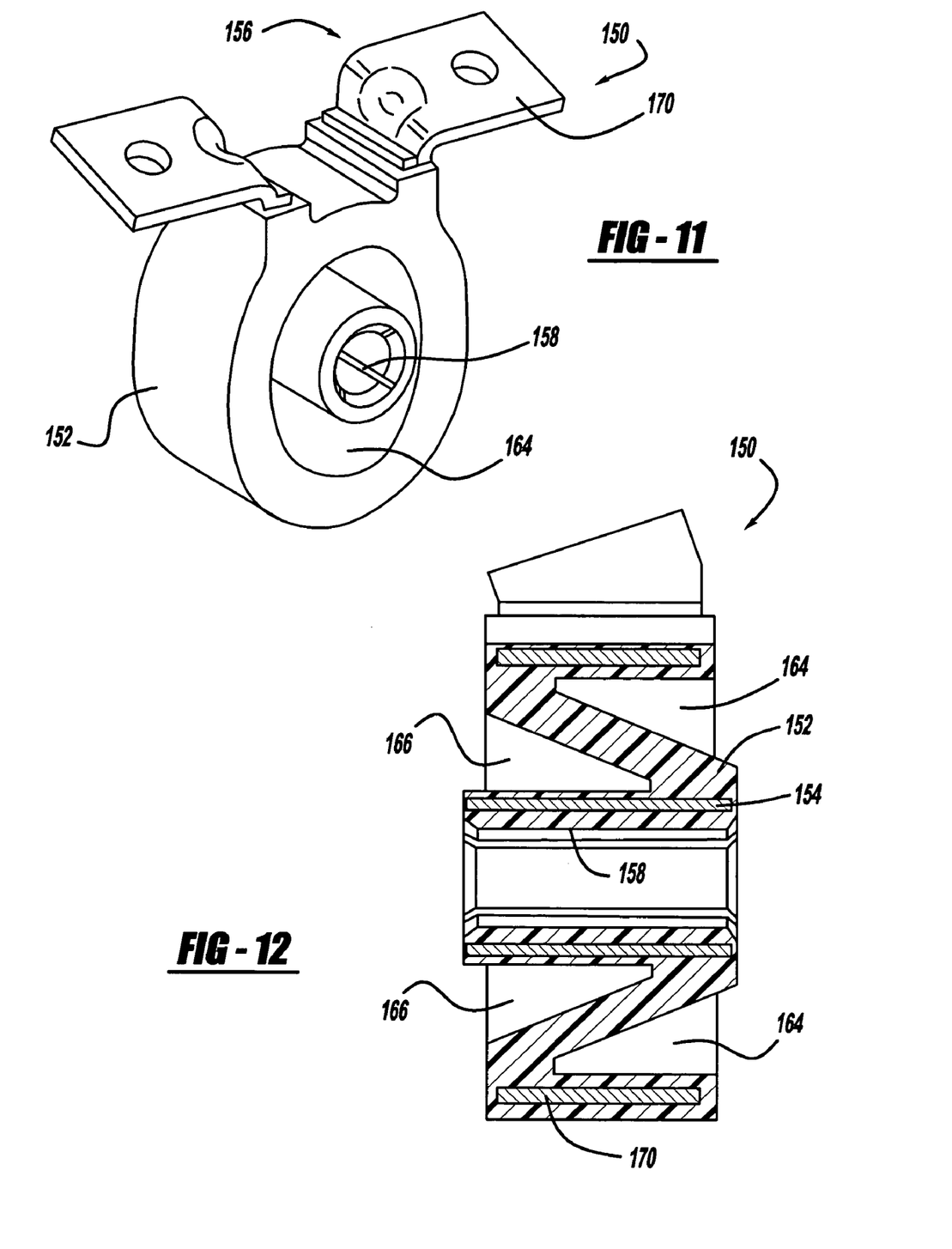
FIG. 11 is a perspective view of an elastomeric isolator in accordance with another embodiment of the present invention.
FIG. 12 is a cross-sectional view of the elastomeric isolator illustrated in FIG. 11.
Figure 13:
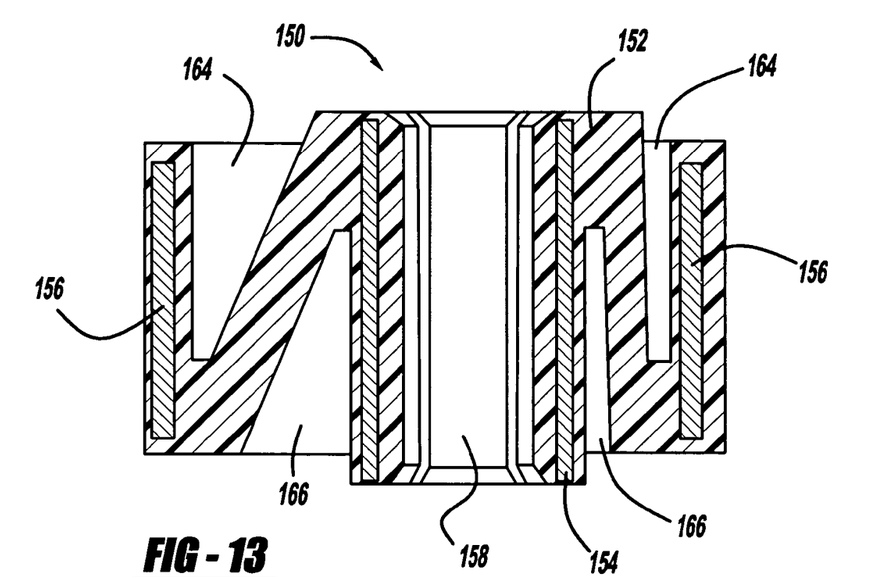
FIG. 13 is a cross-sectional view of the elastomeric isolator illustrated in FIG. 11 taken 90 degrees from the cross-section illustrated in FIG. 12.

Referring now to FIGS. 11-13, an exhaust system isolator 150 in accordance with another embodiment of the present invention is illustrated. Isolator 150 comprises an elastomeric body 152 within which an inner reinforcement 154 and an outer reinforcement 156 are molded. Isolator 150 is a single hole shear hub design where elastomeric body 152 defines a hole 158 which is designed to accept an inner tube or hanger pin 42. Hanger pin 42 is secured to exhaust system 10 and isolator 150 is secured to the frame or the mounting structure of the vehicle using outer reinforcement 156. Thus, exhaust system 10 is secured to the vehicle through isolator 150.

Elastomeric bushing 152 defines an outer circumferential void 164 and an inner circumferential void 166. While voids 164 and 166 are illustrated as asymmetrical with respect to the center of hole 158, it is within the scope of the present invention to have voids 164 and 166 symmetrical with respect to hole 158 if desired. The design of the voids, specifically their thickness, will determine the amount of travel until the rate of the bushing spikes up at the closing of the voids. Until the closing of the voids, the radial loads cause pure shear regardless of the loading direction. Similar to that discussed above for isolator 30, isolator 150 can be loaded in any of the three axial directions as illustrated in FIG. 4. Tuning for rate and deflection in selective directions can be accomplished independently from other directions by altering the voids in the required sectors. As can be seen in FIG. 12, void 164 overlaps with void 166. The larger the overlap between voids 164 and 166, the lower the stresses and stiffness for isolator 60. Voids 164 and 166 are located between inner reinforcement 154 and outer reinforcement 156 such the peak loads bottom out voids 164 and 166 and start to impart compressive stress to elastomeric body 162 from inner reinforcement 164 and outer reinforcement 166 by sandwiching. As illustrated in FIGS. 11-13, outer reinforcement 156 comprises a generally U-shaped bracket 170 which is adapted to be secured to the frame or the mounting structure of the vehicle and a bracket 172 which extends between the two legs or U-shaped bracket 170 and is secured to each leg of U-shaped bracket 170 by crimping or by an other means known in the art. Thus, the bottoming out of voids 164 and 166 and subsequent compression of elastomeric body 152 makes the stress spread out to all of the material between inner reinforcement 154 and outer reinforcement 156 as well as between hanger pin 160 and inner reinforcement 154 rather than having the stress concentrated in a spoke or leg cross-section as in the prior art. This permits the stress magnitude to decrease as well as changing the stress loading to a more favorable type.

Thus, exhaust system isolator 150, similar to isolator 30, provides a very soft on-center rate which is desirable with the ability to endure spike durability loads after closing of the voids.

Figure 14:
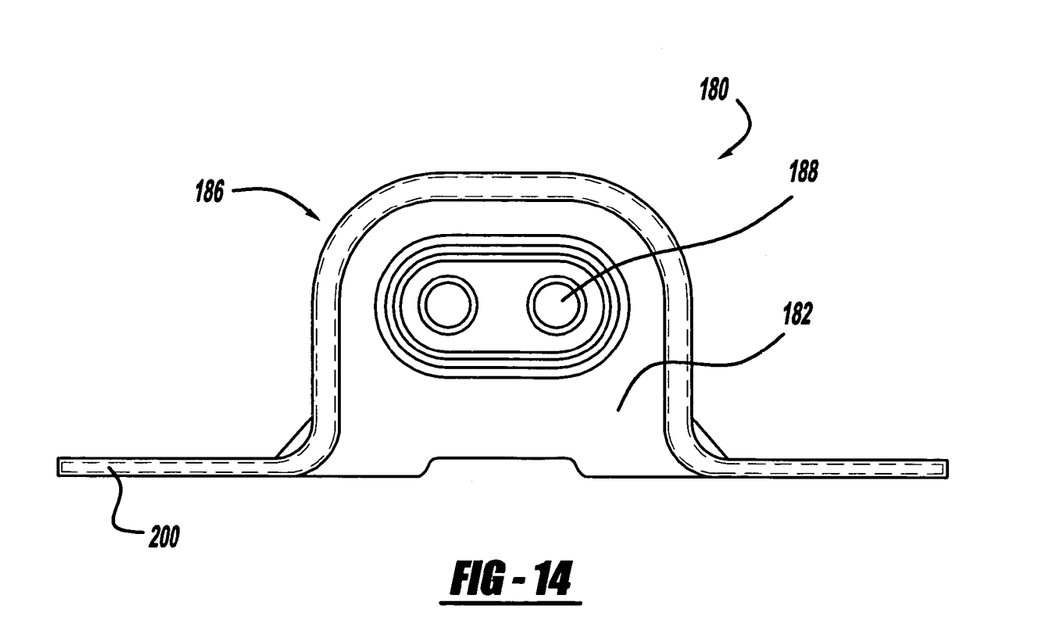
FIG. 14 is a side view of an elastomeric isolator in accordance with another embodiment of the present invention.
Figure 15:
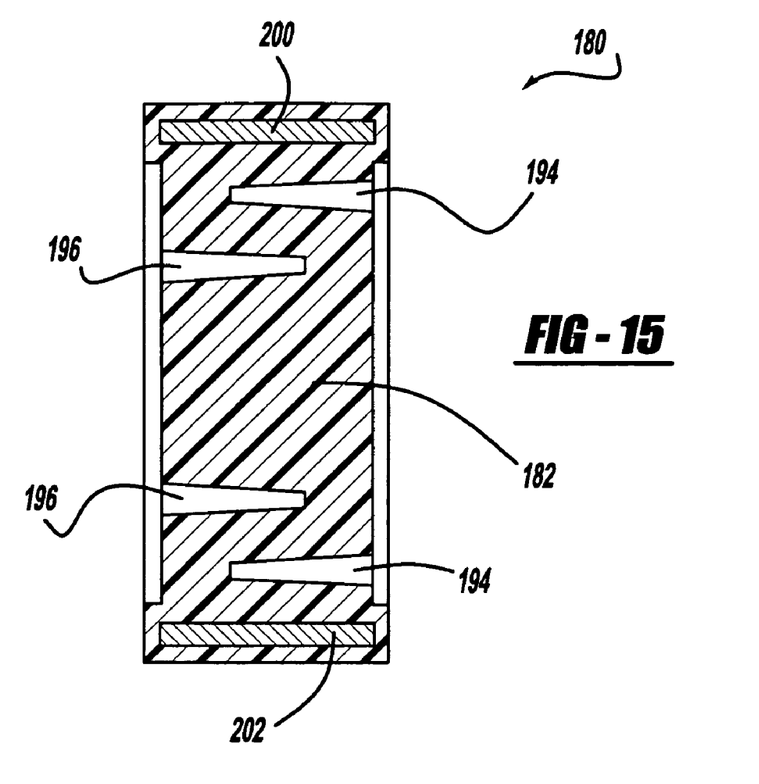
FIG. 15 is a cross-sectional view of the elastomeric isolator illustrated in FIG. 14.
Figure 16:
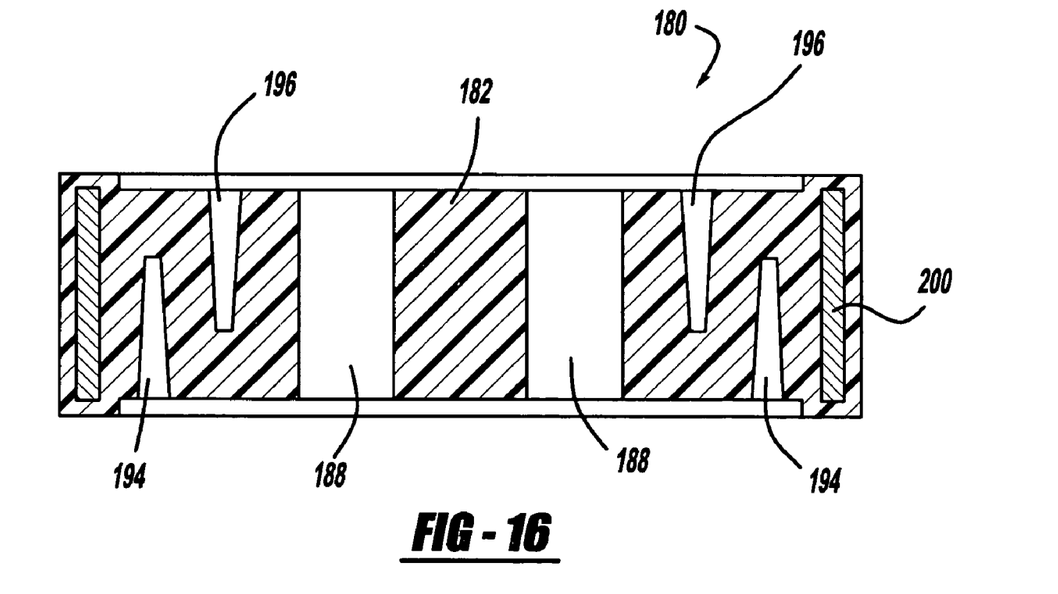
FIG. 16 is a cross-sectional view of the elastomeric isolator illustrated in FIG. 14 taken 90 degrees from the cross-section illustrated in FIG. 15.

Referring now to FIGS. 14-16, an exhaust system isolator 180 in accordance with another embodiment of the present invention is illustrated. Isolator 180 comprises an elastomeric body 182 within which an outer reinforcement 186 is molded. Isolator 180 is a double hole shear hub design where elastomeric body 182 defines a pair of holes 188 each of which are designed to accept an inner tube or hanger pin 42. Hanger pins 42 are secured to exhaust system 10 and isolator 180 is secured to the frame or the mounting structure of the vehicle using outer reinforcement 186. Thus, exhaust system 10 is secured to the vehicle through isolator 180.

Elastomeric bushing 182 defines an outer circumferential void 194 and an inner circumferential void 196. While voids 194 and 196 are illustrated as symmetrical with respect to the center of isolator 180, it is within the scope of the present invention to have voids 194 and 196 asymmetrical with respect to isolator 180 if desired. The design of the voids, specifically their thickness, will determine the amount of travel until the rate of the bushing spikes up at the closing of the voids. Until the closing of the voids, the radial loads cause pure shear regardless of the loading direction. Similar to that discussed above for isolator 30, isolator 180 can be loaded in any of the three axial directions as illustrated in FIG. 4. Tuning for rate and deflection in selective directions can be accomplished independently from other directions by altering the voids in the required sectors. As can be seen in FIG. 16, void 194 overlaps with void 196. The larger the overlap between voids 194 and 196, the lower the stresses and stiffness for isolator 60. Voids 194 and 196 are located within outer reinforcement 186 such the peak loads bottom out voids 194 and 196 and start to impart compressive stress to elastomeric body 192 from hanger pins 42 and outer reinforcement 196 by sandwiching. As illustrated in FIGS. 14-16, outer reinforcement 186 comprises a generally U-shaped bracket 200 which is adapted to be secured to the frame or the mounting structure of the vehicle and a bracket 202 which extends between the two legs or U-shaped bracket 200 and is secured to each leg of U-shaped bracket 200 by crimping or by an other means known in the art. Thus, the bottoming out of voids 194 and 196 and subsequent compression of elastomeric body 182 makes the stress spread out to all of the material between hanger pins 42 and outer reinforcement 186 rather than having the stress concentrated in a spoke or leg cross-section as in the prior art. This permits the stress magnitude to decrease as well as changing the stress loading to a more favorable type.

Thus, exhaust system isolator 180, similar to isolator 30, provides a very soft on-center rate which is desirable with the ability to endure spike durability loads after closing of the voids.

Figures 17, 18:
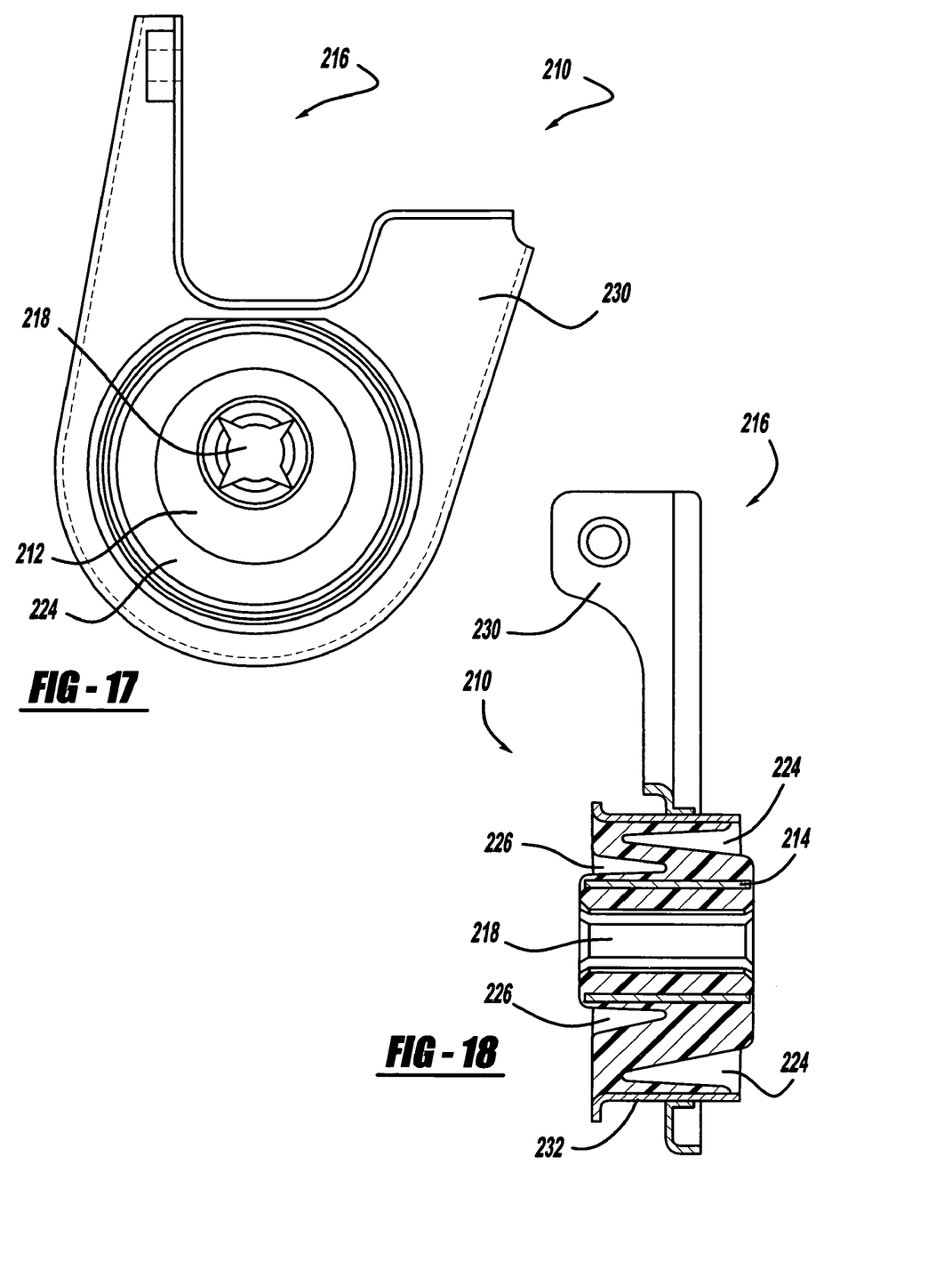
FIG. 17 is a side view of an elastomeric isolator in accordance with another embodiment of the present invention.
FIG. 18 is a cross-sectional view of the elastomeric isolator illustrated in FIG. 17.

Referring now to FIGS. 17 and 18, an exhaust system isolator 210 in accordance with another embodiment of the present invention is illustrated. Isolator 210 comprises an elastomeric body 212 within which an inner reinforcement 214 and an outer reinforcement 216 are molded. Isolator 210 is a single hole shear hub design where elastomeric body 212 defines a hole 218 which is designed to accept an inner tube or hanger pin 42. Hanger pin 42 is secured to exhaust system 10 and isolator 210 is secured to the frame or the mounting structure of the vehicle using outer reinforcement 216. Thus, exhaust system 10 is secured to the vehicle through isolator 210.

Elastomeric bushing 212 defines an outer circumferential void 224 and an inner circumferential void 226. While voids 224 and 226 are illustrated as asymmetrical with respect to the center of hole 218, it is within the scope of the present invention to have voids 224 and 226 symmetrical with respect to hole 218 if desired. The design of the voids, specifically their thickness, will determine the amount of travel until the rate of the bushing spikes up at the closing of the voids. Until the closing of the voids, the radial loads cause pure shear regardless of the loading direction. Similar to that discussed above for isolator 30, isolator 210 can be loaded in any of the three axial directions as illustrated in FIG. 4. Tuning for rate and deflection in selective directions can be accomplished independently from other directions by altering the voids in the required sectors. As can be seen in FIG. 18, void 224 overlaps with void 226. The larger the overlap between voids 224 and 226, the lower the stresses and stiffness for isolator 60. Voids 224 and 226 are located between inner reinforcement 214 and outer reinforcement 216 such the peak loads bottom out voids 224 and 226 and start to impart compressive stress to elastomeric body 222 from inner reinforcement 224 and outer reinforcement 226 by sandwiching. As illustrated in FIGS. 17 and 18, outer reinforcement 216 comprises a generally U-shaped bracket 230 which is adapted to be secured to the frame or the mounting structure of the vehicle and a bracket 232 which is disposed within a bore defined by U-shaped bracket 230 and is secured to U-shaped bracket 230 by a press fitting or by an other means known in the art. Thus, the bottoming out of voids 224 and 226 and subsequent compression of elastomeric body 212 makes the stress spread out to all of the material between inner reinforcement 214 and outer reinforcement 216 as well as between hanger pin 42 and inner reinforcement 214 rather than having the stress concentrated in a spoke or leg cross-section as in the prior art. This permits the stress magnitude to decrease as well as changing the stress loading to a more favorable type.

Thus, exhaust system isolator 210, similar to isolator 30, provides a very soft on-center rate which is desirable with the ability to endure spike durability loads after closing of the voids.

Figure 19:
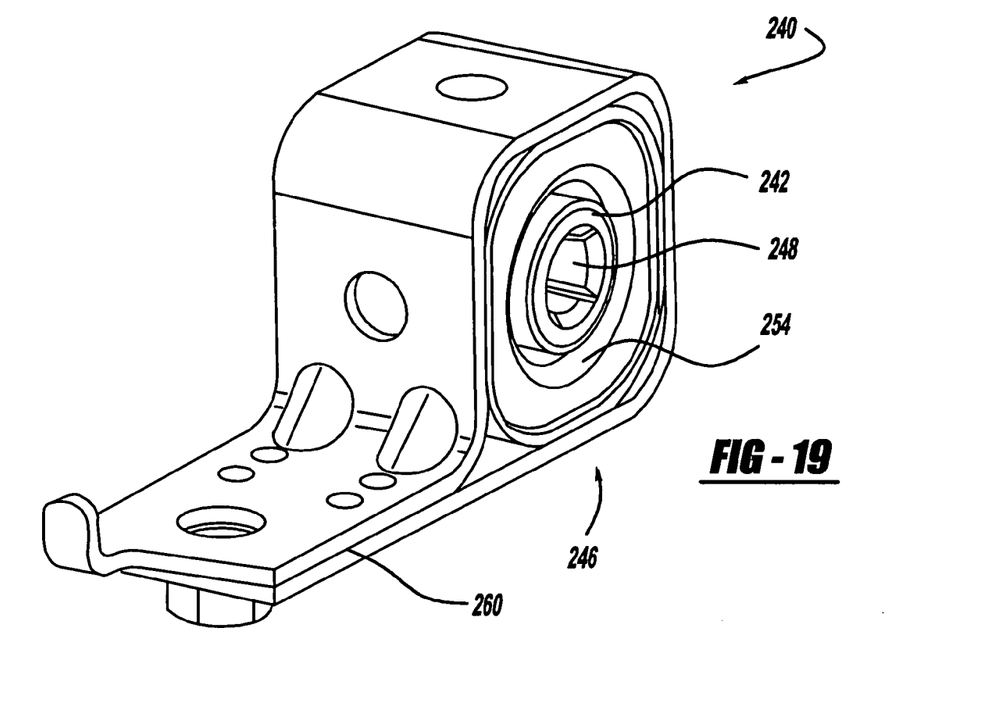
FIG. 19 is a perspective view of an elastomeric isolator in accordance with another embodiment of the present invention.
Figure 20:
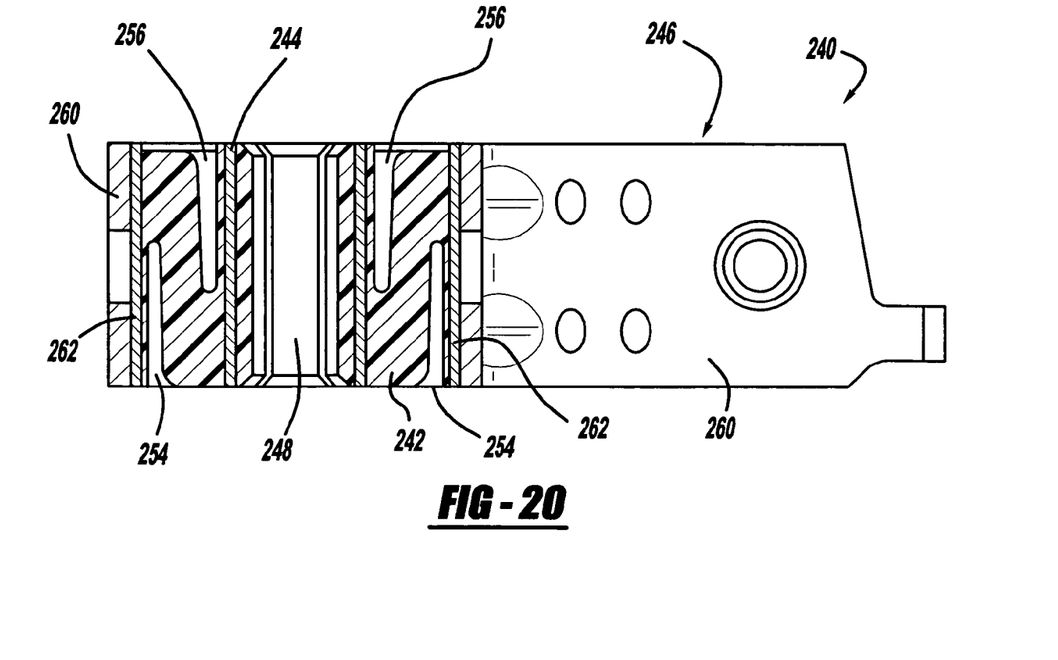
FIG. 20 is a cross-sectional view of the elastomeric isolator illustrated in FIG. 19.

Referring now to FIGS. 19 and 20, an exhaust system isolator 240 in accordance with another embodiment of the present invention is illustrated. Isolator 240 comprises an elastomeric body 242 within which an inner reinforcement 244 and an outer reinforcement 246 are molded. Isolator 240 is a single hole shear hub design where elastomeric body 242 defines a hole 248 which is designed to accept an inner tube or hanger pin 42. Hanger pin 42 is secured to exhaust system 10 and isolator 240 is secured to the frame or the mounting structure of the vehicle using outer reinforcement 246. Thus, exhaust system 10 is secured to the vehicle through isolator 240.

Elastomeric bushing 242 defines an outer circumferential void 254 and an inner circumferential void 256. While voids 254 and 256 are illustrated as symmetrical with respect to the center of hole 248, it is within the scope of the present invention to have voids 254 and 256 asymmetrical with respect to hole 248 if desired. The design of the voids, specifically their thickness, will determine the amount of travel until the rate of the bushing spikes up at the closing of the voids. Until the closing of the voids, the radial loads cause pure shear regardless of the loading direction. Similar to that discussed above for isolator 30, isolator 240 can be loaded in any of the three axial directions. Tuning for rate and deflection in selective directions can be accomplished independently from other directions by altering the voids in the required sectors. As can be seen in FIG. 20, void 254 overlaps with void 256. The larger the overlap between voids 254 and 256, the lower the stresses and stiffness for isolator 60. Voids 254 and 256 are located between inner reinforcement 244 and outer reinforcement 246 such the peak loads bottom out voids 254 and 256 and start to impart compressive stress to elastomeric body 252 from inner reinforcement 254 and outer reinforcement 256 by sandwiching. As illustrated in FIGS. 19 and 20, outer reinforcement 246 comprises a generally rectangular shaped bracket 260 which is adapted to be secured to the frame or the mounting structure of the vehicle and a bracket 262 which extends around the periphery of elastomeric body 252. Thus, the bottoming out of voids 254 and 256 and subsequent compression of elastomeric body 242 makes the stress spread out to all of the material between inner reinforcement 244 and outer reinforcement 246 as well as between hanger pin 42 and inner reinforcement 244 rather than having the stress concentrated in a spoke or leg cross-section as in the prior art. This permits the stress magnitude to decrease as well as changing the stress loading to a more favorable type.

Thus, exhaust system isolator 240, similar to isolator 30, provides a very soft on-center rate which is desirable with the ability to endure spike durability loads after closing of the voids.

Figures 21, 22:
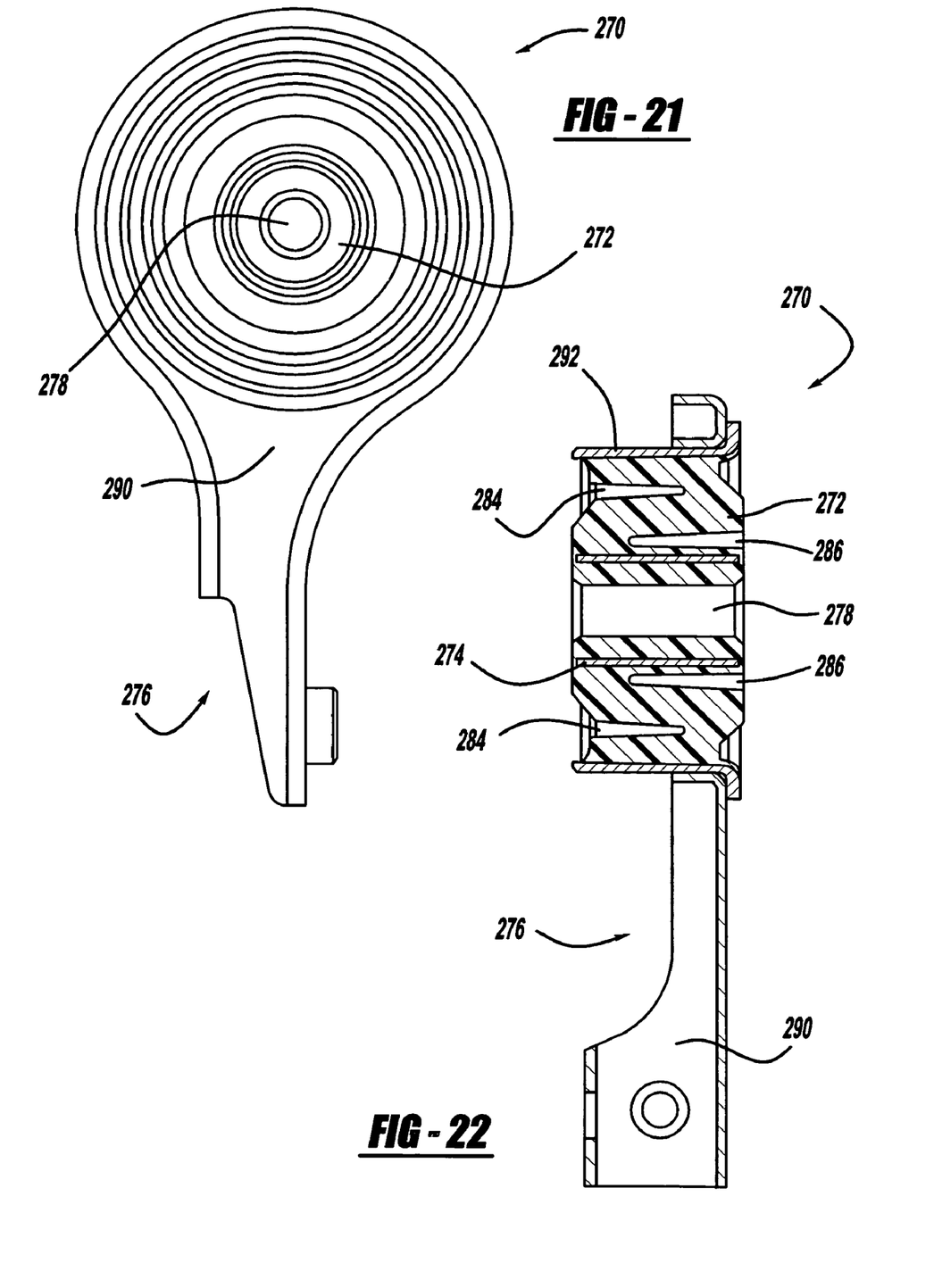
FIG. 21 is a side view of an elastomeric isolator in accordance with another embodiment of the present invention.
FIG. 22 is a cross-sectional view of the elastomeric isolator illustrated in FIG. 21.

Referring now to FIGS. 21 and 22, an exhaust system isolator 270 in accordance with another embodiment of the present invention is illustrated. Isolator 270 comprises an elastomeric body 272 within which an inner reinforcement 274 and an outer reinforcement 276 are molded. Isolator 270 is a single hole shear hub design where elastomeric body 272 defines a hole 278 which is designed to accept an inner tube or hanger pin 42. Hanger pin 42 is secured to exhaust system 10 and isolator 270 is secured to the frame or the mounting structure of the vehicle using outer reinforcement 276. Thus, exhaust system 10 is secured to the vehicle through isolator 270.

Elastomeric bushing 272 defines an outer circumferential void 284 and an inner circumferential void 286. While voids 284 and 286 are illustrated as symmetrical with respect to the center of hole 278, it is within the scope of the present invention to have voids 284 and 286 asymmetrical with respect to hole 278 if desired. The design of the voids, specifically their thickness, will determine the amount of travel until the rate of the bushing spikes up at the closing of the voids. Until the closing of the voids, the radial loads cause pure shear regardless of the loading direction. Similar to that discussed above for isolator 30, isolator 270 can be loaded in any of the three axial directions. Tuning for rate and deflection in selective directions can be accomplished independently from other directions by altering the voids in the required sectors. As can be seen in FIG. 22, void 284 overlaps with void 286. The larger the overlap between voids 284 and 286, the lower the stresses and stiffness for isolator 60. Voids 284 and 286 are located between inner reinforcement 274 and outer reinforcement 276 such the peak loads bottom out voids 284 and 286 and start to impart compressive stress to elastomeric body 282 from inner reinforcement 274 and outer reinforcement 276 by sandwiching. As illustrated in FIGS. 21 and 22, outer reinforcement 276 comprises a bracket 290 which is adapted to be secured to the frame or the mounting structure of the vehicle and a bracket 292 which is disposed within a bore defined by bracket 290 and is secured to bracket 290 by press fitting or by an other means known in the art. Thus, the bottoming out of voids 284 and 286 and subsequent compression of elastomeric body 272 makes the stress spread out to all of the material between inner reinforcement 274 and outer reinforcement 276 as well as between hanger pin 42 and inner reinforcement 274 rather than having the stress concentrated in a spoke or leg cross-section as in the prior art. This permits the stress magnitude to decrease as well as changing the stress loading to a more favorable type.

Thus, exhaust system isolator 270, similar to isolator 30, provides a very soft on-center rate which is desirable with the ability to endure spike durability loads after closing of the voids.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. An isolator comprising:
   an elastomeric body;
   a first member defined by the elastomeric body for attaching the elastomeric body to a first component;
   a second member for attaching the elastomeric body to a second component; wherein
   the elastomeric body defines a first annular void encircling only the first member, the first annular void extending in a first direction into the elastomeric body from an outer surface of a first side of the elastomeric body;
   the elastomeric body defines a second annular void encircling only the first member, the second annular void extending in a second direction opposite to the first direction into the elastomeric body from an outer surface of a second side of the elastomeric body opposite to the first side;
   the first annular void overlaps the second annular void by a specified overlap in an overlap direction generally perpendicular to the first direction.

2. The isolator according to claim 1, wherein said first member comprises a first hole extending through said elastomeric body generally parallel to the first direction.

3. The isolator according to claim 2, wherein said second member is a second hole extending through said elastomeric body generally parallel to the first direction.

4. The isolator according to claim 3, further comprising an insert disposed within the elastomeric body, the insert encircling the first and second annular voids.

5. The isolator according to claim 4, wherein the insert encircles the first and second hole.

6. The isolator according to claim 2, further comprising an insert disposed within the elastomeric body, the insert encircling the first hole.

7. The isolator according to claim 2, wherein said second member is a bracket disposed around the first and second voids.

8. The isolator according to claim 7, further comprising an insert disposed within the elastomeric body, the insert encircling the first hole.

9. The isolator according to claim 2, wherein said second member is a pair of holes extending through the elastomeric body generally parallel to the first direction.

10. The isolator according to claim 9, further comprising an insert disposed within the elastomeric body, the insert encircling the first hole.

11. The isolator according to claim 1, wherein said second member is a bracket disposed around the first and second voids.

12. The isolator according to claim 1, further comprising an insert disposed within the elastomeric body, the insert encircling the first hole.

13. The isolator according to claim 1, wherein said second member comprises a pair of holes extending through said elastomeric body generally parallel to the first direction.

14. The isolator according to claim 13, wherein said second member is a bracket disposed around the first and second voids.

15. The isolator according to claim 1, wherein the first annular void is asymmetric in relation to the first member.

16. The isolator according to claim 15, wherein the second annular void is asymmetric in relation to the first member.

17. The isolator according to claim 1, wherein the first annular void is concentric with the first member.

18. The isolator according to claim 17, wherein the second annular void is concentric with the first member.

19. The isolator according to claim 1, further comprising an insert disposed within the elastomeric body, the insert encircling the first and second member and encircling the first and second annular void.

* * * * *

UNITED STATES PATENT AND TRADEMARK OFFICE
CERTIFICATE OF CORRECTION

PATENT NO. : 7,644,911 B2
APPLICATION NO. : 11/233283
DATED : January 12, 2010
INVENTOR(S) : Troy P. Rodecker It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1116 days.

Signed and Sealed this

Twenty-first Day of December, 2010

David J. Kappos
*Director of the United States Patent and Trademark Office*